United States Patent
Martinez et al.

(10) Patent No.: US 6,889,103 B2
(45) Date of Patent: *May 3, 2005

(54) SYSTEMS AND METHODS FOR REALTIME DETERMINATION OF ASPHALT CONTENT

(75) Inventors: David Frederick Martinez, Cypress, TX (US); Elias George ElDahdah, Houston, TX (US)

(73) Assignee: Atser, Houston, TX (US)

( * ) Notice: Subject to any disclaimer, the term of this patent is extended or adjusted under 35 U.S.C. 154(b) by 19 days.

This patent is subject to a terminal disclaimer.

(21) Appl. No.: 10/224,668

(22) Filed: Aug. 22, 2002

(65) Prior Publication Data

US 2004/0039467 A1 Feb. 26, 2004

(51) Int. Cl.⁷ .............................................. G06F 19/00
(52) U.S. Cl. .............................. 700/97; 702/83; 73/824

(58) Field of Search ........................ 700/97, 117, 265; 73/824, 863.11; 436/155, 157; 702/84, 83

(56) References Cited

U.S. PATENT DOCUMENTS

| | | | |
|---|---|---|---|
| 5,943,234 A | | 8/1999 | Martinez et al. |
| 6,436,718 B1 | * | 8/2002 | Troxler ...................... 436/155 |
| 6,711,957 B2 | * | 3/2004 | Martinez et al. .............. 73/824 |

* cited by examiner

*Primary Examiner*—Leo Picard
*Assistant Examiner*—Steven R. Garland
(74) *Attorney, Agent, or Firm*—Tran & Associates

(57) ABSTRACT

Systems and methods are disclosed for automating mix design by estimating volumetric properties for one or more mix designs; running one or more tests on the mix design using a gyratory compactor; digitally collecting data for each gyration from the gyratory compactor; selecting an optimum mix based on the gyration data; and testing a sample of the optimum mix using an ignition process.

12 Claims, 3 Drawing Sheets

SYSTEMS AND METHODS FOR REALTIME DETERMINATION OF ASPHALT CONTENT

BACKGROUND

The invention relates to determine asphalt content of a hot mix sample.

A test method has been developed by the National Center of Asphalt Technology (NCAT) to determine the asphalt content of hot mix asphalt by ignition (1990 sponsored by FHWA). This test method is an alternative replaced The Chlorinated solvents test which is not environmentally safe to use it is an ozone depleting compounds and the US environmental protection agency's in 1990 clean air Act Amendments discontinuation of trichloroethane production after Dec. 31, 1995, in addition to environmental risks these solvent are expensive and difficult to dispose.

Other method Nuclear Asphalt Content (NAC) gives rapid results of Asphalt Content by using the nuclear gauge but do not allow the determination of aggregate gradation of the hot mix.

Other method Biodegradable solvent can be used but they are time consuming, and disposal of the solvent are not safe environmentally.

Finally 1994 the (NCAT) ignition method which use a furnace to ignite the asphalt cement. 1200 grams of hot mix is subjected to an elevated temperature of 538 C in a furnace to ignite and burn the asphalt cement the process take 30 to 40 minutes and the aggregate gradation can then be determined using standard sieve analysis.

DESCRIPTION

Figure 1:
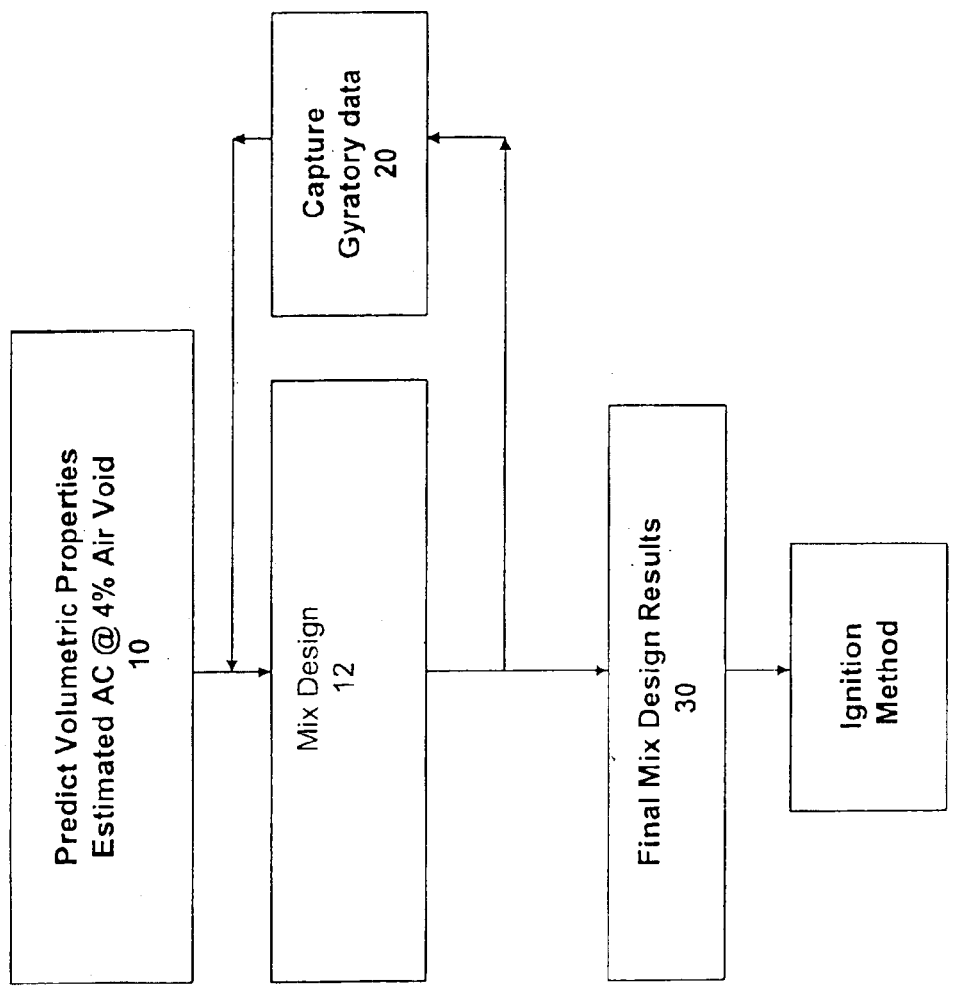
FIG. 1 shows a process for designing asphalt mixtures.

FIG. 1 shows a process for designing an asphalt mixture. First, volumetric properties are estimated (10). Next, a mix is designed (12). The mix can be the Superpave mix. During this process, gyratory data is automatically collected (20). The final mix is optimized (30). Next, samples are mixed and processed using a control ignition method (40).

In one embodiment where the sample is 2000 grams of asphalt mix, the ignition method test procedure is as follows:

1) Weight the Sample and basket before ignition @ (149C (300F), grams.
2) Tare weight of Basket @ (149C (300F), grams.
3) Weight of Sample before ignition @ 149C (300F), grams. [1-2]
4) Calculate 0.02% of Initial Sample Weight.
5) Weight the Sample and basket after $1^{st}$ Burn @ 149C (300F), grams.
6) Weight of Sample After 1st Burn @ 149C (300F), grams. [5-2]
7) Weight of Sample and basket After 2nd Burn @ 149C (300F), grams.
8) Weight of Sample After 2nd Burn @ 149C (300F), grams. [7-2]
9) Difference Between weight 1st & $2^{nd}$ Burns, grams [6-8].
10) If [9]<[4], Else run an other Burn till condition satisfied.

Total Weight Loss @ 149C (300F) After Ignition, grams ([3-6]+ [3-8])/2

Weight Loss=$(Wi-Wf)$ grams

Asphalt Content %=$100*(Wi-Wf)/Wi$

11) Aggregate remaining is used to determine gradation.

Figure 2:
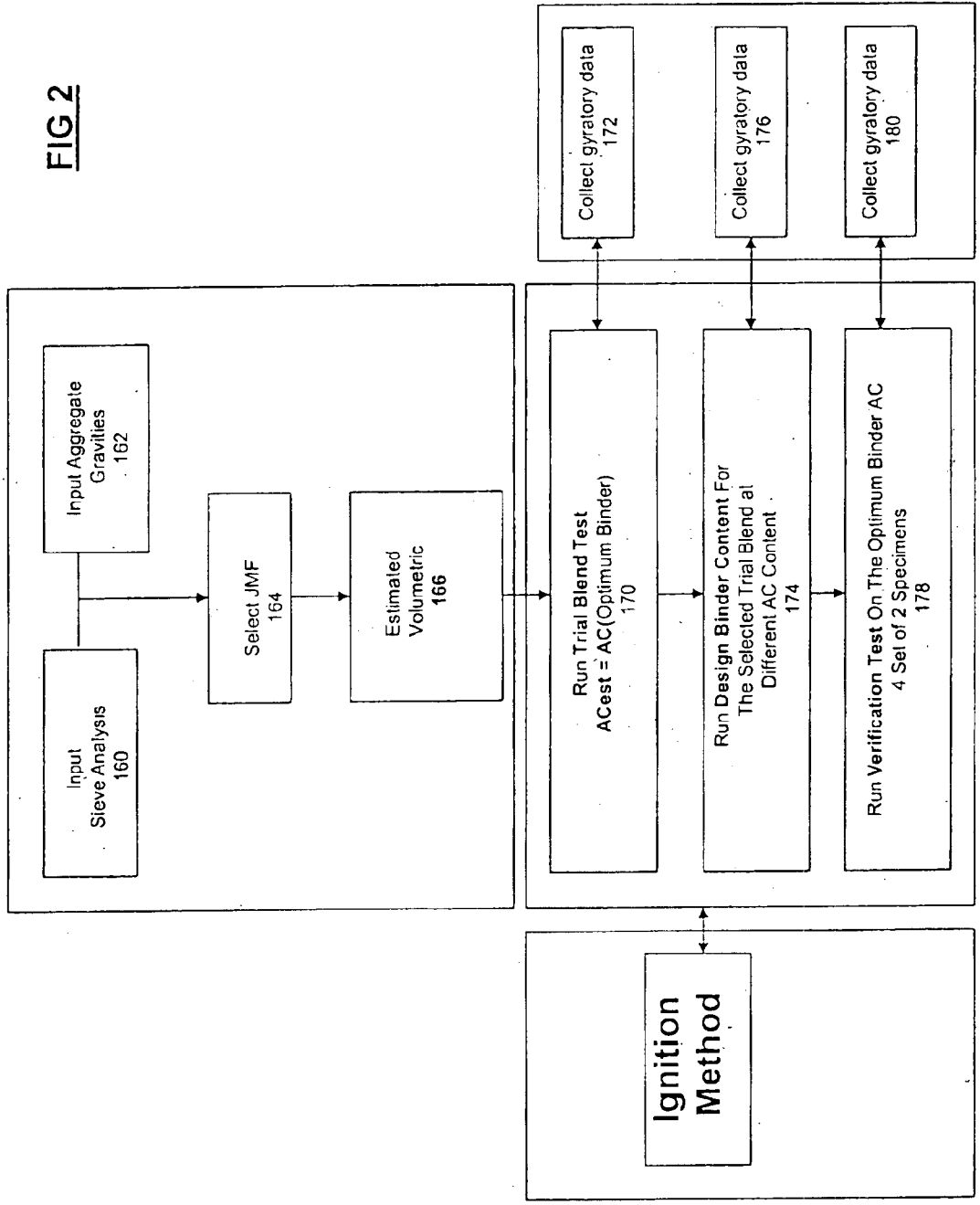
FIG. 2 shows one embodiment of the process of FIG. 1.

Referring now to FIG. 2, one embodiment for estimating mixture design is illustrated in more detail. The inputs to the process of FIG. 2 include performing sieve analysis (160) and inputting gravities data (162). The inputs received from blocks 160 and 162 are used to select a job mix formulation (JMF) (164). A variety of tools, including a graphical data entry tool, a computer optimized data entry tool, a forced data entry tool, and the manual data entry tool, are provided to select the JMF in block 164. Promising JMFs could be quickly evaluated using the estimation process provided by the present invention. JMFs which do not promote compliance of desired specifications can be quickly eliminated from expensive laboratory testing, saving the user time, labor and money. Thus, the present invention uses basic engineering properties to evaluate the proposed JMF and to test the proposed JMF for verification of the desired volumetric properties and to optimize the binder content. The present invention thereby allows the user to rapidly determine whether the proposed JMF, including the combination of aggregates and asphalts that defines the actual gradation and asphalt content to be obtained in the finished construction, satisfies the mixture design. The output of the JMF selection block 164 is provided to estimate volumetric properties with estimated AC Content @4% Air Void (166).

Next, the process of FIG. 2 performs laboratory verification of various proposed JMF solutions that may satisfy the requirements. First, a trial blend test is run based on estimated AC Content @4% Air Void (170). The test uses data collected by a compactor control process of FIG. 1 (172). Based on the trial blend test, a trial blend is selected.

A design binder content test is run for the selected trial blend (174). The content test requests the process of FIG. 1 to generate gyratory data for the selected trial blend (176). Based on the design Binder Content test, an optimum binder is selected. From this selection, a verification test is run on the optimum binder (178). The verification test uses new gyratory data for the optimum binder.

Next, an illustrative Superpave Level I Mix Design procedure is discussed. By, asphalt and aggregate materials that meet their respective criteria are selected. The asphalt binders performance specification is based on the climate and attendant pavement temperatures in which the binder is expected to serve. Physical property requirements remain the same, but the temperature at which the binder must attain the properties change. The aggregate physical properties may be specified as coarse aggregate angularity, fine aggregate angularity, flat elongated particles, or by clay content, for example. Several trial blends are generated to meet Superpave gradation requirements (Coarse,Intermediate, Fine). Superpave uses the 0.45 power gradation chart with control limits and a restricted zone to develop a design aggregate structure. The aggregate Blend gradation may pass between the control points while avoiding the restricted zone. The maximum density gradation is drawn from 00% passing the maximum aggregate size through the origin.

Asphalt is blended with trial blends aggregate and run gyratory trial blend. Based on the volumetric test results, the best blend meeting the Superpave Level I Specification is selected.

Gyratory compaction test for the selected trial aggregate blend is performed with various design binder contents, and calculate the optimum binder at, for example, a 4% Air void from volumetric test results. Another exemplary aggregate design process is detailed below:

1. Two specimens for each trial blend at estimated AC content (4% air void Target) are compacted using the superpave gyratory compactor. And specimens are also prepared for determination of the mixture maximum theoretical specific gravity Gmm (AASHTO T209).
2. Specimens are mixed at the appropriate temperature (165° C. to 172° C.) for the selected PG58-34 Binder. Specimens then short aged by placing the loose mix in a flat pan, in a forced draft oven at 135° C., for 4 hours. The specimens are then brought to compaction temperature range (151° C. to 157° C.). By placing them in another oven for short time less than 30 minutes.

The specimens are then removed and either
   a) Compacted.
   b) Allowed to cool loose for max theoretical specific gravity determination.
3. The number of gyrations used for compaction is determined based on the design high air temperature of the paving location and the traffic level, (ex. 38° C. 10–30 ESAL millions) The number of gyrations

---

| | |
|---|---|
| @ Ninitial = | 8 gyrations |
| @ Ndesign = | 109 gyrations |
| @ Nmax = | 174 gyrations |

---

4. Each specimen will be compacted to the max number of gyrations with data is collected during the compaction process. (FIG. 1).
5. Knowing the initial mass of the mix. The fixed diameter of the mold, and the measured height, the density can be continually monitored.
6. After compaction, the final density of the specimen is determined by AASHTO T166.
7. The Gmm of each blend is also determined by AASHTO T209.
8. % Gmm (percent of maximum theoretical density) at each gyration can be determined, and corrected to match the final measured density of that specimen.

Volumetric Properties Determinations:

---

Volume: $V = 0.001 \times h \times 3.14 \times d^2/4$
density: $Gmb_{(estimated)} = 100 \times W/V$
Correction factor $C_{correct} = Gmb_{(measured)}/Gmb_{(estimated@Nmax)}$
Correct density: $Gmb_{(correct)} = C_{correct} \times Gmb_{(measured)}$
Percent of maximum theoretical density:
$\% Gmm_{(correct)} = Gmb_{(correct)}/Gmm_{(measured)}$
Air Void: $V_a = 100 - \% Gmm_{(correct)}$ @Ndesign
$VMA_{est} = 100 - \% Gmm_{(correct)}$ @Ndesign $\times Gmm_{(measured)} \times (100 - ACest)/100 \times Gsb)$

---

V: volume of specimen
h: height of specimen
d: diameter of mold.
W: weight of specimen.
Gsb: aggregates Bulk Specific gravity 9. From the first (AC estimate) most on the time we cannot reach (4% Air Void). A second (AC estimate) is recalculated using correction factor. And Volumetric Properties are recalculated.

$\% AC_{(estimated\ @4\%\ Va)} = AC_{est} - 0.4 \times (4 - Va)$
$\% ACeff_{(estimated\ @4\%\ Va)} = \% AC_{(estimated\ @4\%\ Va)} - (100 - \% AC_{(estimated\ @4\%\ Va)}) \times Gs \times (Gse - Gsb)/(Gse \times Gsb)$
Dust Proportion: $DP = (\% P200)/(\% ACeff_{(estimated\ @4\%\ Va)})$
$VMA_{(est.@4\%\ Va)} = \% VMA_{est} + C \times (4 - Va)$
$C = 0.1$ if $Va <= 4.0$
$C = 0.2$ if $Va > 4.0$
$VFA_{(est.@4\%\ Va)} = 100 \times (VMA_{(est.@4\%\ Va)} - 4)/VMA_{(est.@4\%\ Va)}$
$\% Gmm_{(est.@4\%\ Va)(correct@Nini)} = \% Gmm_{(trial)(correct@Nini)} - (4 - Va)$
$\% Gmm_{(est.@4\%\ Va)(correct@Nmax)} = \% Gmm_{(trial)(correct@Nmax)} - (4 - Va)$ 10. Check SUPERPAVE Level I Criteria for VMA, VFA, DP, $\% Gmm_{@ini}$, $\% Gmm_{@Nmax}$.

Select the best blend that pass the criteria, and run design binder content at:

[AC−0.5], [AC], [AC+1], [AC+0.5]

11. Two specimens for each AC content are compacted using the superpave gyratory compactor and the process of FIG. 2. And specimens are also prepared for determination of the mixture maximum theoretical specific gravity Gmm (AASHTO T209).
12. Volumetric Properties are calculated @ each AC content, and Optimum Binder is calculated @ 4% airVoid. The volumetric properties are checked against the Criteria for SUPERPAVE Level I.
13. Densification Curves are plotted for every specimen from the collected data using the process of FIG. 2.

(X=Number of Gyration, Y=% Gmm)

Figure 3:
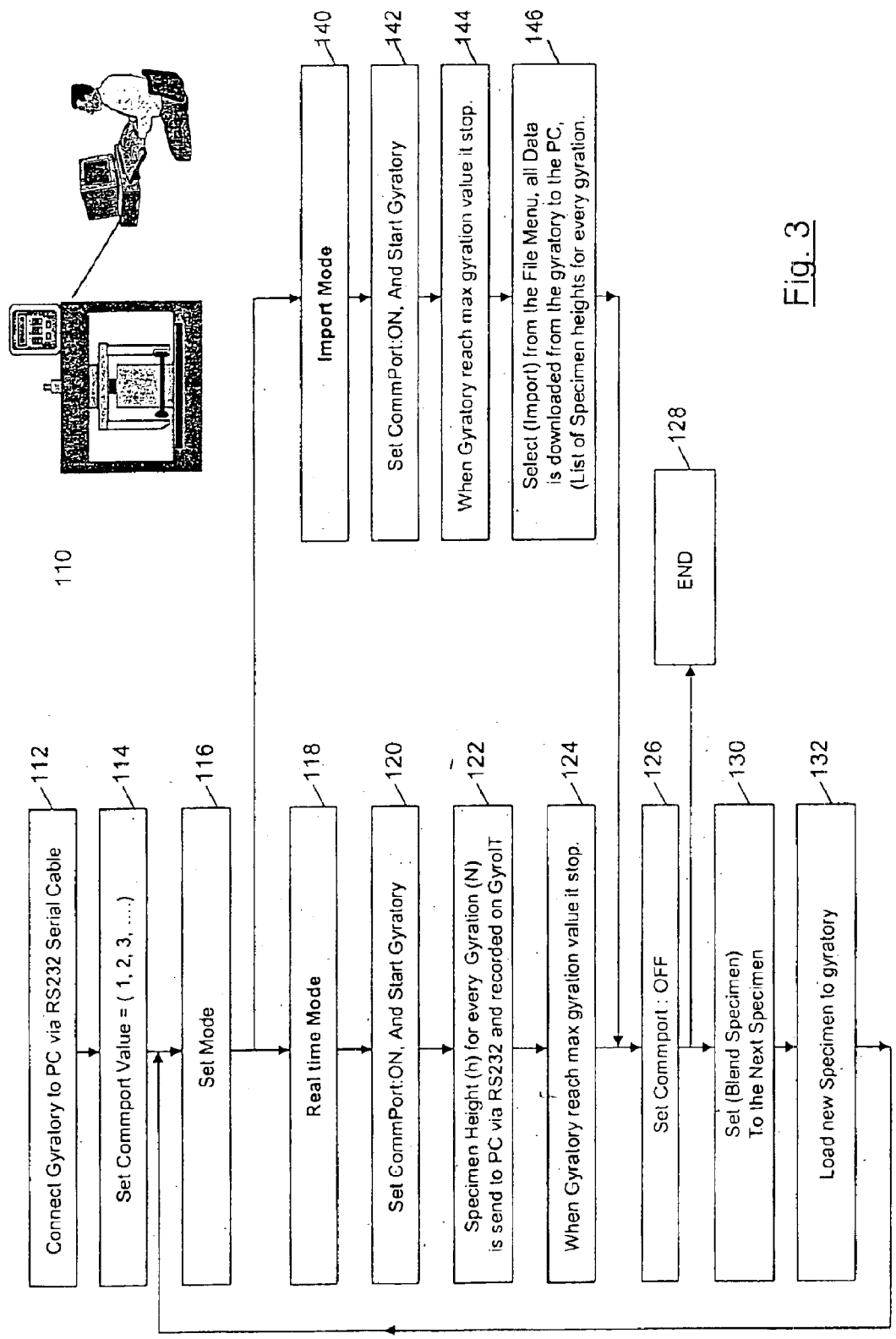
FIG. 3 shows a process for performing gyratory compaction and collecting gyratory data to be used in the process of FIG. 2.

FIG. 3 shows a process 110 for performing gyratory compaction and collecting gyratory data to be used in the process of FIG. 2. First, the user selects a gyratory equipment type (112). The equipment can be a unit commercially available from a variety of vendors, Pine Instrument Company of Grove City, Pa.; and Troxler Electronic Laboratories, Inc. of Research Triangle Park, N.C. Next, the user sets up communications port with the selected equipment (114). The user selects a display mode: Real Time or Import from a file (116). If the user selects Real Time mode (118), the process 110 turns on the communication port and starts the gyratory compactor/equipment (120). Next, the gyratory compactor measures a specimen height for each gyration and the resulting information is captured (122). When the gyratory compactor reaches a predetermined maximum gyration value, the gyratory compactor is turned off (124). Next, the communication port is turned off (126).

The process 110 then determines whether another specimen needs to be tested. If not, the process 110 exits (128). Alternatively, the next specimen is selected (130) and the new specimen is loaded into the gyratory compactor (132). The process then loops back to allow the user to set the mode (116). From the mode selection (116), the user can select an import mode (140). In this mode, the communication port is turned on and the gyratory compactor is started (142). The process monitors the gyratory compactor and when the maximum gyration value is reached, the process stops (144). Data stored in the gyratory compactor is captured (146) and downloaded for volumetric properties calculation. Next, the process 110 jumps to 124 and turns off the gyratory compactor.

The above processes can be implemented as software running on a computer. The preferred software embodiment worlds with Microsoft's Windows operating system, including Windows-98, Windows-NT and Windows-XP, although any other suitable graphical operating system such as MacOS and Solaris can be used. Windows is a graphical-based operating environment, also known as a graphical user interface, or (GUI) that allows multitasking of programs. In Windows, the computer screen operates like a desktop, allowing instantaneous access to clocks, spreadsheets, word processing, communication software, graphics packages and, of course, this mix design program. The user is able to select rapidly among those applications, as well as any others developed for the environment. The ability to work simultaneously on several different projects more closely approximates the manner in which most people work. However, the user can work in one program at a time if desired. Preferably, the software of the invention is an object-oriented software constructed from Visual Basic, although it can be written in a number of other languages.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for automating mix design, comprising:
   estimating volumetric properties for one or more mix designs;
   running one or more tests on the mix design using a gyratory compactor;
   digitally collecting data for each gyration from the gyratory compactor;
   selecting an optimum mix based on the gyration data; and
   testing a sample of the optimum mix.

2. The method of claim 1, further comprising determining the weight of the sample.

3. The method of claim 2, further comprising burning a first portion of the sample and determining the weight of the first burned sample.

4. The method of claim 3, further comprising burning a second portion of the sample and determining the weight of the second burned sample.

5. The method of claim 4, further comprising comparing the weights of the first and second burned samples to determine whether the weights conform to a predetermined tolerance.

6. The method of claim 4, further comprising determining a weight loss for one of the first and second burned samples.

7. The method of claim 6, further comprising determining asphalt content using the determined weight loss.

8. The method of claim 6, further comprising determining gradation of the mix.

9. A method for asphalt mix design, comprising:
   predicting properties associated with a mix of volumetric properties;
   verifying properties of the mix by digitally collecting data for each gyration from a gyratory compactor;
   selecting an optimum mix based on the gyration data;
   testing properties of the optimum mix with an ignition process; and
   determining gradation of the optimum mix.

10. The method of claim 9, wherein the mix is a Superpave mix.

11. A system, comprising:
    a gyratory compactor;
    a computer coupled to the gyratory compactor, the computer having computer readable code to estimate volumetric properties for one or more mix designs; run one or more tests on the mix design using the gyratory compactor; digitally collect data for each gyration from the gyratory compactor; and select an optimum mix based on the gyration data; and
    an asphalt content tester coupled to the computer to provide ignition data to test the mix.

12. The system of claim 11, wherein the mix comprises a Superpave mix.

* * * * *